(12) United States Patent
Hanson

(10) Patent No.: US 12,116,599 B2
(45) Date of Patent: Oct. 15, 2024

(54) COMPUTATIONAL REDUCTION VACCINE FOR COVID-19 BIN100

(71) Applicant: Matthew Vernon Hanson, Cambridge, MA (US)

(72) Inventor: Matthew Vernon Hanson, Cambridge, MA (US)

( * ) Notice: Subject to any disclaimer, the term of this patent is extended or adjusted under 35 U.S.C. 154(b) by 445 days.

(21) Appl. No.: 17/138,065

(22) Filed: Dec. 30, 2020

(65) Prior Publication Data

US 2021/0403880 A1      Dec. 30, 2021

Related U.S. Application Data

(60) Provisional application No. 63/045,101, filed on Jun. 27, 2020.

(51) Int. Cl.
*C12N 7/00*          (2006.01)

(52) U.S. Cl.
CPC ...... *C12N 7/00* (2013.01); *C12N 2770/20021* (2013.01); *C12N 2770/20022* (2013.01); *C12N 2770/20034* (2013.01)

(58) Field of Classification Search
None
See application file for complete search history.

(56) References Cited

PUBLICATIONS

GenBank accession PP346416.1 (Feb. 29, 2024) (Year: 2024).*
Genbank accession PP413571 (Feb. 29, 2024) (Year: 2024).*
Lueking, et al. Front Genet. Sep. 26, 2022;13:942713. doi: 10.3389/fgene.2022.942713. PMID: 36226173. (Year: 2022).*

* cited by examiner

*Primary Examiner* — Benjamin P Blumel
*Assistant Examiner* — Jeffrey Mark Sifford

(57) ABSTRACT

A system for the rapid development of vaccines or antibacterial drugs is required when working with pandemics. The easiest way to formulate these new vaccines is through computational reduction of existing organisms via statistical models. Once vaccine candidates are arrived at through this method, "Super Organisms" containing all of the computationally reducible fragments can then be taken through a Crispr reduction process wherein those computationally reducible fragments are removed. The result is a vaccine candidate which has possible problematic function partially or fully removed. The "neutered" version of the virus can be tested in a lab and in clinical trials for efficacy. This patent covers a vaccine candidate utilizing computationally reducible fragments 100 base pairs or greater in length; those fragments removed from future Covid-19 Super Organisms either collectively or individually; as well as the RNA transcripts of those fragments.

3 Claims, 3 Drawing Sheets

Specification includes a Sequence Listing.

Figure 1

COMPUTATIONAL REDUCTION VACCINE FOR COVID-19 BIN100

BACKGROUND OF THE INVENTION

The present invention focuses on a computational reduction vaccine for Covid-19 with reduction fragments larger than 100 base pairs.

A computational reduction vaccine may be defined herein as a vaccine candidate which is arrived at by removing various non-repetitive fragments in a virus or bacteria first computationally, then via Crispr in a "Super-Organism" (an organism which contains all, or the majority, of those fragments), and then utilizing the remaining organism as a traditional "live" or "dead" vaccine, which even though marginally computationally reduced, is still recognizable by the human immune system as an invader and therefore provokes a useful immune response. That immune response then shields the recipient from the actual virus going forward.

It is now possible via Python modules such as Numpy (numerical Python) and Biopython (a module specifically designed for computationally manipulating DNA sequences), to analyze in great detail and with great speed thousands, or even millions of sequence records available through the NIH GenBank databases.

Those computational methods are not herein described, but the statistical analysis below will illustrate the efficacy of the method in determining the frequency of various structures, as well as the ability to track those structures though time. It is along those two lines-frequency of appearance, and consistency of appearance, across an entire genetic database that one can derive vaccine candidates computationally.

The traditional way to do this would be to remove each fragment or structure via Crispr one by one and test the resulting organism for problematic function. Once problematic function was discovered, use the resulting live or dead virus in a vaccine. However, in the case of Covid-19, where solutions are demanded in shorter time frames, it is more efficient to simply remove all potential problematic function fragments via various fragment length groups in order to create one or two potential vaccine candidates instead of hundreds. This is the first of two such vaccines.

BRIEF DESCRIPTION OF SEVERAL VIEWS OF THE DRAWINGS

FIG. 1 is a table of computational fragment reductions from Covid-19 which are longer than 100 base pairs. From left to right, you have the "SEQ ID NO:" indicating the sequence ID in the sequence file; "Bin" size, or size of the fragments; the number of appearances of the fragment across the entire Covid-19 database; the appearance percent of the fragment expressed as a decimal; the Record ID for the reference organism in which the fragment was first found; the "strip" or fragment which when removed from a Covid-19 Super Organism or Base Organism will give us a vaccine; and the location of the fragment in the "Base Organism" relative to MT520215.1.

DETAILED DESCRIPTION OF THE INVENTION

Figure 2:
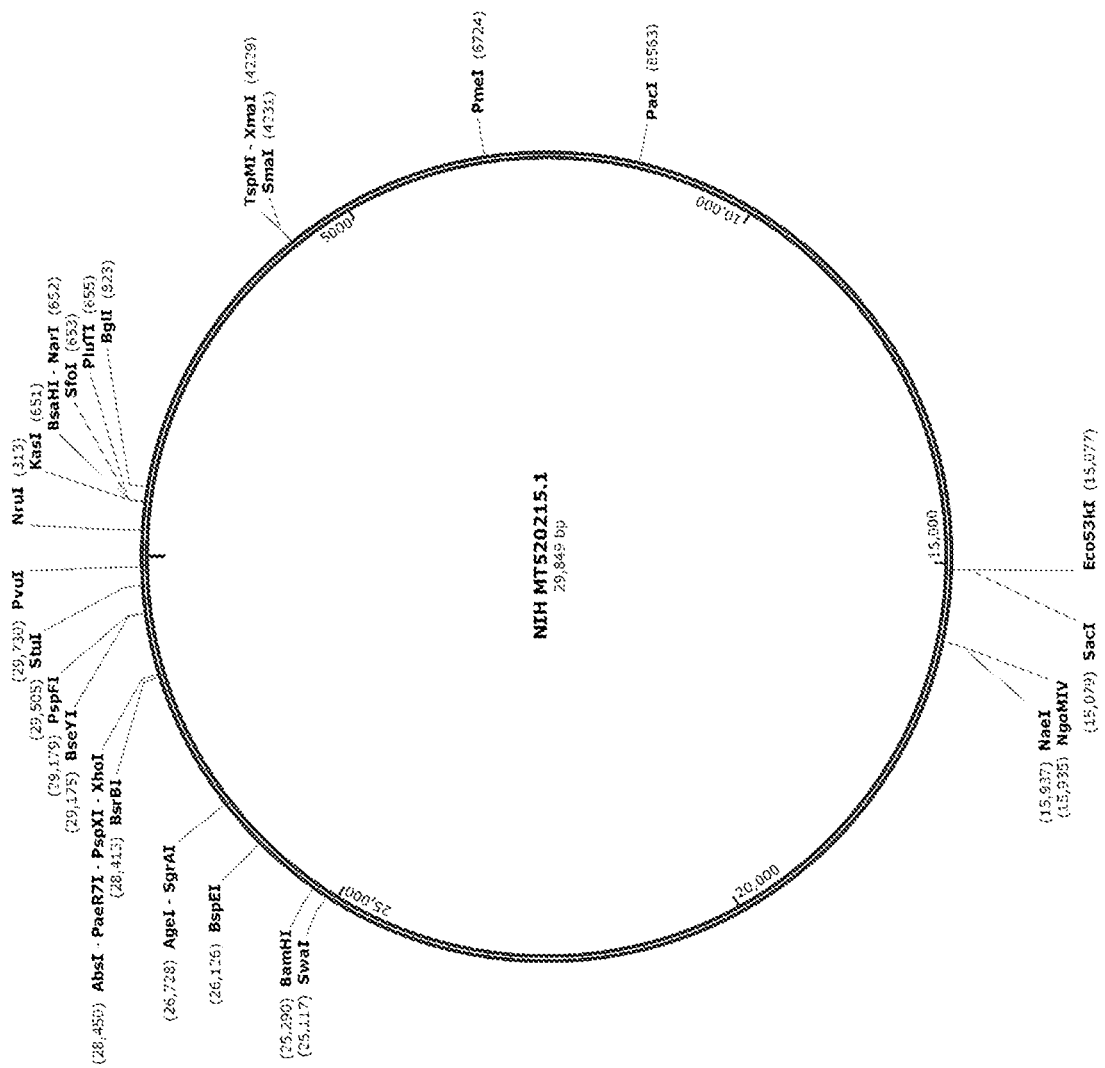
FIG. 2 is a SnapGene circular view of Covid-19 sample MT520215.1 from which this vaccine is derived.
Figure 3:
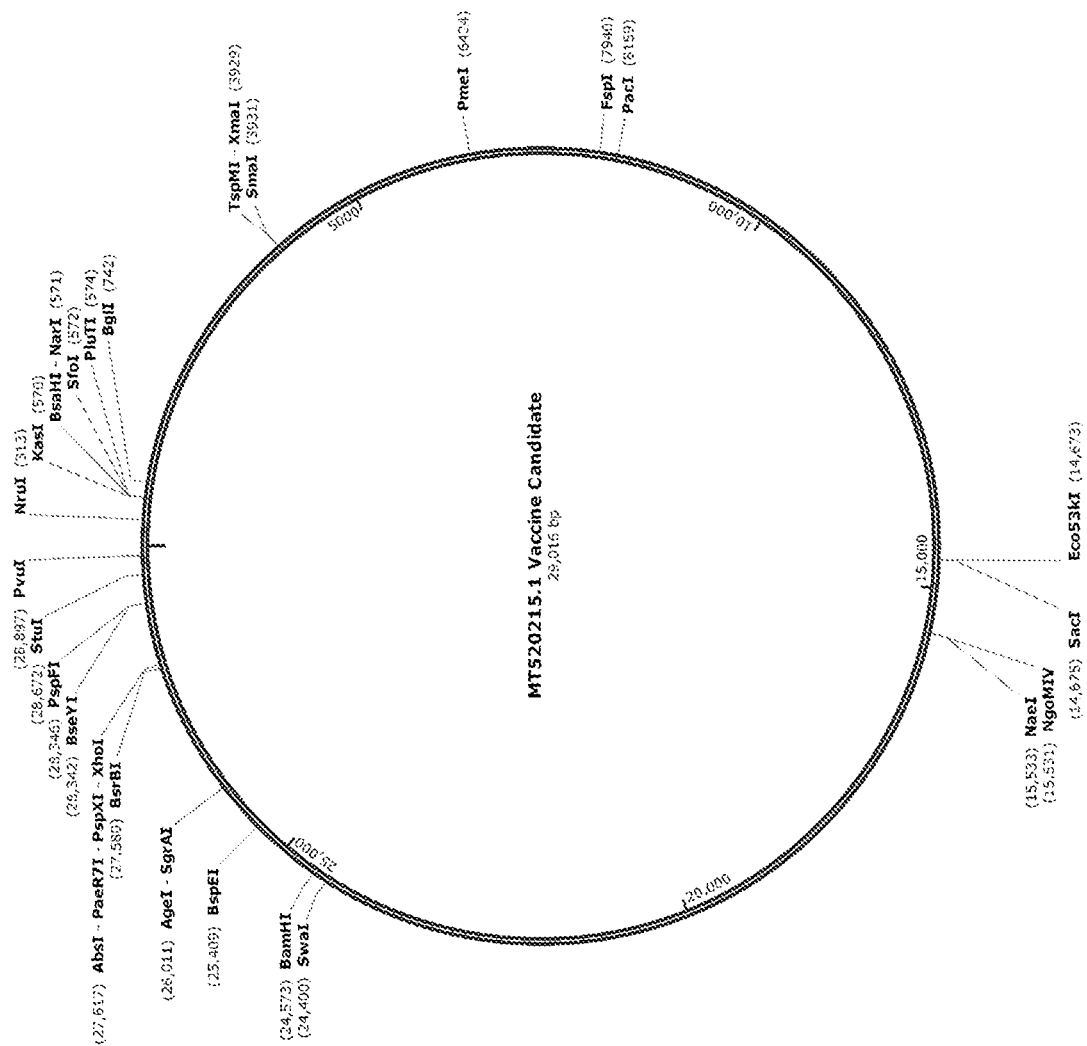
FIG. 3 is the same SnapGene circular view of MT520215.1 with the fragments removed.

There are several types of vaccines. This invention introduces a new type of vaccine which is a computationally derived reductive vaccine. A computationally derived reductive vaccine utilizes statistical computation to arrive at a list of fragments which can then be removed from live viruses or bacteria via Crispr to arrive at "neutered" versions which can then form the basis for the vaccine.

Computational reduction in this case may be defined as non-laboratory computational reduction of organisms into fragments, which then can be assessed on the basis of frequency across an entire range of similar organisms as well as computationally tested to confirm that those structures are unique to the virus or bacteria in question. The particulars of the method of discovery for these fragments is proprietary.

Figure 1:
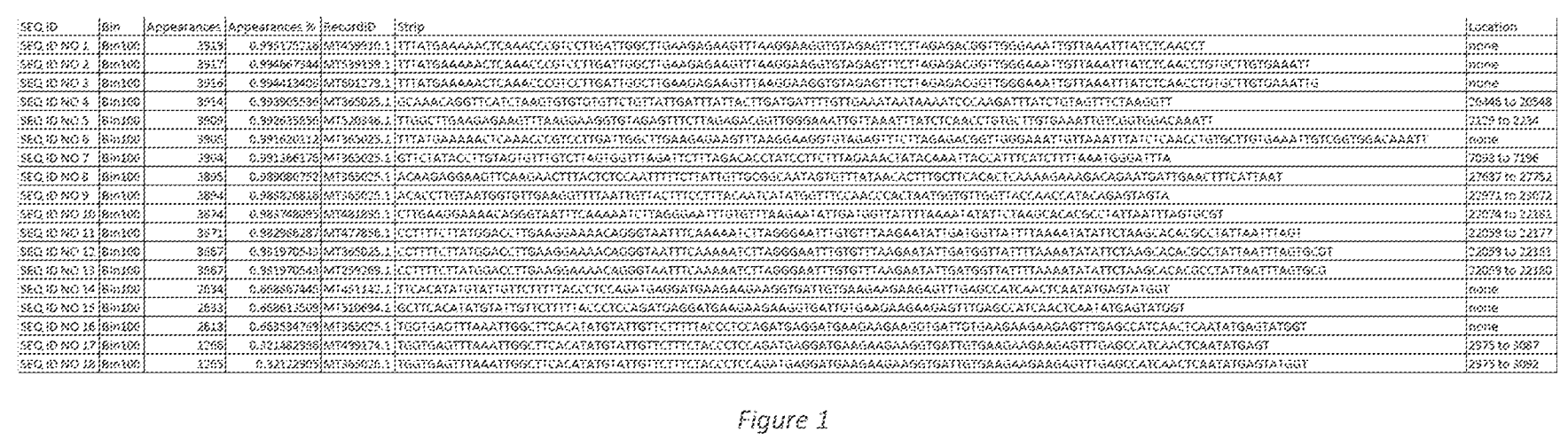

What is not proprietary is the statistical analysis of the fragments which are outlined in FIG. 1 and below. In the case of this particular vaccine candidate, the fragments which are included are longer than 100 base-pairs and appear in the NIH Covid-19 database greater than 32% of the time. The Covid-19 database "snapshot" from which the fragments in this patent were selected was taken on Jun. 16, 2020 at 5:21 am. That database is available upon request.

The result of this patent is relatively simple. When a "Super Organism" or Covid-19 sample which contains all, or most, of the fragments outlined below is found, that Super Organism can then be genetically modified in a laboratory using Crispr to remove those fragments. Once all those fragments are removed from the organism, it can then be tested to see if problematic function remains. "Problematic function" in the case of Covid-19 is two-fold: functions of the virus which cause high transmissibility rates, and functions of the virus which cause high mortality rates. It may take us years to figure out exactly what those functions are and where they appear exactly on the genetic assay. This patent provides a shortcut by simply removing all of the most likely candidates for those problematic functions by identifying fragments which appear often enough not to be considered mutations (i.e. fragments only appearing in one or two samples).

The scan of the entire database of Covid-19 provides 18 fragments longer than 100 base pairs which appear more than 32% of the time across the entire database. These fragments are unique to Covid-19 and cannot be found in any other virus in the NIH GenBank databases.

Additionally, it is possible to state that the most likely vaccine candidate fragments in more targeted versions of this patent are Fragments 14-16, as they appear in approximately 70% of the database, but not in nearly all samples which would include early (non-transmissible, low-fatality) Covid-19 organisms.

In creation of the vaccine candidate we can also view that vaccine not only as a reductive entity which can be manufactured from a variety of possible starting organisms, but also as a complete organism which has potentially been "neutered" of its destructive features.

In order to arrive at that possibility, we must first find a Covid-19 sample which contains all of these structures. Of the 3,938 complete Covid-19 sequences in the Jun. 16, 2020 Covid-19 database, there are 2,467 which contain the maximum of 16 of the 18 of those sequences. However, since there is some overlap between fragments, only 7 need be removed.

So to create a reductive vaccine, computationally those fragments are removed to create the vaccine candidate as shown in SEQ ID NO: 37. The original reference can be downloaded from NIH via the reference MT520215.1. As previously stated, there are also 2,467 other reference candidates which could be used as Super Organisms or Base Organisms for the next generation of vaccines. That list is available upon request.

This application also seeks to cover the RNA transcript of each of the fragments (SEQ ID NOs: 19-36). It may well be that RNA transcript vaccines based on these fragments would be of equal or greater efficacy in triggering a useful immune response.

It should also be noted that these fragments are 100 base pairs or greater, which means a fragment has only a 1 in 1.60 novemdecillion ($4^{100}$) chance of occurring—in the entire history of the planet. In other words, even at a 32% recurrence rate across the entire Covid-19 genome, these fragments represent viable mathematical targets for vaccines.

This application identifies 18 such fragments.

SEQUENCE LISTING

```
<160> NUMBER OF SEQ ID NOS: 37

<210> SEQ ID NO 1
<211> LENGTH: 105
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT459910.1.

<400> SEQUENCE: 1
tttatgaaaa actcaaaccc gtccttgatt ggcttgaaga gaagtttaag gaaggtgtag        60
agtttcttag agacggttgg gaaattgtta aatttatctc aacct                      105

<210> SEQ ID NO 2
<211> LENGTH: 119
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT539159.1.

<400> SEQUENCE: 2
tttatgaaaa actcaaaccc gtccttgatt ggcttgaaga gaagtttaag gaaggtgtag        60
agtttcttag agacggttgg gaaattgtta aatttatctc aacctgtgct tgtgaaatt       119

<210> SEQ ID NO 3
<211> LENGTH: 120
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT601279.1.

<400> SEQUENCE: 3
tttatgaaaa actcaaaccc gtccttgatt ggcttgaaga gaagtttaag gaaggtgtag        60
agtttcttag agacggttgg gaaattgtta aatttatctc aacctgtgct tgtgaaattg      120

<210> SEQ ID NO 4
<211> LENGTH: 103
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT365025.1.

<400> SEQUENCE: 4
gcaaacaggt tcatctaagt gtgtgtgttc tgttattgat ttattacttg atgattttgt        60
tgaaataata aaatcccaag atttatctgt agtttctaag gtt                        103

<210> SEQ ID NO 5
```

```
<211> LENGTH: 106
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT520346.1.

<400> SEQUENCE: 5
ttggcttgaa gagaagttta aggaaggtgt agagtttctt agagacggtt gggaaattgt      60
taaatttatc tcaacctgtg cttgtgaaat tgtcggtgga caaatt                    106

<210> SEQ ID NO 6
<211> LENGTH: 134
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT365025.1.

<400> SEQUENCE: 6
tttatgaaaa actcaaaccc gtccttgatt ggcttgaaga gaagtttaag gaaggtgtag      60
agtttcttag agacggttgg gaaattgtta aatttatctc aacctgtgct tgtgaaattg     120
tcggtggaca aatt                                                       134

<210> SEQ ID NO 7
<211> LENGTH: 104
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT365025.1.

<400> SEQUENCE: 7
gttctatacc ttgtagtgtt tgtcttagtg gtttagattc tttagacacc tatccttctt      60
tagaaactat acaaattacc atttcatctt ttaaatggga ttta                      104

<210> SEQ ID NO 8
<211> LENGTH: 116
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT365025.1.

<400> SEQUENCE: 8
acaagaggaa gttcaagaac tttactctcc aatttttctt attgttgcgg caatagtgtt      60
tataacactt tgcttcacac tcaaaagaaa gacagaatga ttgaactttc attaat         116

<210> SEQ ID NO 9
<211> LENGTH: 102
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT365025.1.

<400> SEQUENCE: 9
acaccttgta atggtgttga aggttttaat tgttactttc ctttacaatc atatggtttc      60
caacccacta atggtgttgg ttaccaacca tacagagtag ta                        102
```

```
<210> SEQ ID NO 10
<211> LENGTH: 108
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT481895.1.

<400> SEQUENCE: 10
cttgaaggaa aacagggtaa tttcaaaaat cttagggaat tgtgtttaa gaatattgat        60 ggttatttta aaatatattc taagcacacg cctattaatt tagtgcgt                  108

<210> SEQ ID NO 11
<211> LENGTH: 119
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT477856.1.

<400> SEQUENCE: 11 cctttctta tggaccttga aggaaaacag ggtaatttca aaaatcttag ggaatttgtg        60
tttaagaata ttgatggtta ttttaaaata tattctaagc acacgcctat taatttagt      119

<210> SEQ ID NO 12
<211> LENGTH: 123
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT365025.1.

<400> SEQUENCE: 12 cctttctta tggaccttga aggaaaacag ggtaatttca aaaatcttag ggaatttgtg        60
tttaagaata ttgatggtta ttttaaaata tattctaagc acacgcctat taatttagtg     120
cgt                                                                    123

<210> SEQ ID NO 13
<211> LENGTH: 122
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT259269.1.

<400> SEQUENCE: 13 cctttctta tggaccttga aggaaaacag ggtaatttca aaaatcttag ggaatttgtg        60
tttaagaata ttgatggtta ttttaaaata tattctaagc acacgcctat taatttagtg     120
cg                                                                     122

<210> SEQ ID NO 14
<211> LENGTH: 100
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT451142.1.
```

<400> SEQUENCE: 14
ttcacatatg tattgttctt tttaccctcc agatgaggat gaagaagaag gtgattgtga    60
agaagaagag tttgagccat caactcaata tgagtatggt                          100

<210> SEQ ID NO 15
<211> LENGTH: 102
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT510694.1.

<400> SEQUENCE: 15
gcttcacata tgtattgttc tttttacccct ccagatgagg atgaagaaga aggtgattgt    60
gaagaagaag agtttgagcc atcaactcaa tatgagtatg gt                       102

<210> SEQ ID NO 16
<211> LENGTH: 118
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT365025.1.

<400> SEQUENCE: 16
tggtgagttt aaattggctt cacatatgta ttgttctttt taccctccag atgaggatga    60
agaagaaggt gattgtgaag aagaagagtt tgagccatca actcaatatg agtatggt     118

<210> SEQ ID NO 17
<211> LENGTH: 113
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT499174.1.

<400> SEQUENCE: 17
tggtgagttt aaattggctt cacatatgta ttgttctttc taccctccag atgaggatga    60
agaagaaggt gattgtgaag aagaagagtt tgagccatca actcaatatg agt           113

<210> SEQ ID NO 18
<211> LENGTH: 118
<212> TYPE: DNA
<213> ORGANISM: Artificial Sequence
<220> FEATURE:
<223> OTHER INFORMATION: SEQ ID NOs 1-18 are DNA fragments found in a
      wide variety of Covid-19 samples (see Specification). This
      fragment was originally scanned from NIH ID: MT365026.1.

<400> SEQUENCE: 18
tggtgagttt aaattggctt cacatatgta ttgttctttc taccctccag atgaggatga    60
agaagaaggt gattgtgaag aagaagagtt tgagccatca actcaatatg agtatggt     118

<210> SEQ ID NO 19
<211> LENGTH: 105
<212> TYPE: RNA
<213> ORGANISM: Artificial Sequence
<220> FEATURE:
<223> OTHER INFORMATION: SEQ ID NOs 19-36 are the mRNA transcriptions of
      SEQ ID NOs 1-18.

<400> SEQUENCE: 19
uuuaugaaaa acucaaaccc guccuugauu ggcuugaaga gaaguuuaag gaagguguag      60
aguuucuuag agacgguugg gaaauuguua aauuuaucuc aaccu                     105

<210> SEQ ID NO 20
<211> LENGTH: 119
<212> TYPE: RNA
<213> ORGANISM: Artificial Sequence
<220> FEATURE:
<223> OTHER INFORMATION: SEQ ID NOs 19-36 are the mRNA transcriptions of
      SEQ ID NOs 1-18.

<400> SEQUENCE: 20
uuuaugaaaa acucaaaccc guccuugauu ggcuugaaga gaaguuuaag gaagguguag      60
aguuucuuag agacgguugg gaaauuguua aauuuaucuc aaccugugcu ugugaaauu      119

<210> SEQ ID NO 21
<211> LENGTH: 120
<212> TYPE: RNA
<213> ORGANISM: Artificial Sequence
<220> FEATURE:
<223> OTHER INFORMATION: SEQ ID NOs 19-36 are the mRNA transcriptions of
      SEQ ID NOs 1-18.

<400> SEQUENCE: 21
uuuaugaaaa acucaaaccc guccuugauu ggcuugaaga gaaguuuaag gaagguguag      60
aguuucuuag agacgguugg gaaauuguua aauuuaucuc aaccugugcu ugugaaauug     120

<210> SEQ ID NO 22
<211> LENGTH: 103
<212> TYPE: RNA
<213> ORGANISM: Artificial Sequence
<220> FEATURE:
<223> OTHER INFORMATION: SEQ ID NOs 19-36 are the mRNA transcriptions of
      SEQ ID NOs 1-18.

<400> SEQUENCE: 22
gcaaacaggu ucaucuaagu gugugucuuc uguuauugau uuauuacuug augauuugu       60 ugaaauaaua aaaucccaag auuuaucugu aguuucaag guu                        103

<210> SEQ ID NO 23
<211> LENGTH: 106
<212> TYPE: RNA
<213> ORGANISM: Artificial Sequence
<220> FEATURE:
<223> OTHER INFORMATION: SEQ ID NOs 19-36 are the mRNA transcriptions of
      SEQ ID NOs 1-18.

<400> SEQUENCE: 23
uuggcuugaa gagaaguuua aggaaggugu agaguuucuu agagacgguu gggaaauugu      60
uaaauuuauc ucaaccugug cuugugaaau gucggugga caaauu                     106

<210> SEQ ID NO 24
<211> LENGTH: 134
<212> TYPE: RNA
<213> ORGANISM: Artificial Sequence
<220> FEATURE:
<223> OTHER INFORMATION: SEQ ID NOs 19-36 are the mRNA transcriptions of
      SEQ ID NOs 1-18.

<400> SEQUENCE: 24
uuuaugaaaa acucaaaccc guccuugauu ggcuugaaga gaaguuuaag gaagguguag      60

```
aguuucuuag agacgguugg gaaauuguua aauuuaucuc aaccugugcu ugugaaauug    120
ucgguggaca aauu                                                     134

<210> SEQ ID NO 25
<211> LENGTH: 104
<212> TYPE: RNA
<213> ORGANISM: Artificial Sequence
<220> FEATURE:
<223> OTHER INFORMATION: SEQ ID NOs 19-36 are the mRNA transcriptions of
      SEQ ID NOs 1-18.

<400> SEQUENCE: 25
guucuauacc uuguagυguu ugcuuagug guuuagauuc uuuagacacc uauccuucuu     60
uagaaacuau acaaauuacc auuucaucuu uuaaauggga uuua                    104

<210> SEQ ID NO 26
<211> LENGTH: 116
<212> TYPE: RNA
<213> ORGANISM: Artificial Sequence
<220> FEATURE:
<223> OTHER INFORMATION: SEQ ID NOs 19-36 are the mRNA transcriptions of
      SEQ ID NOs 1-18.

<400> SEQUENCE: 26
acaagaggaa guucaagaac uuuacucucc aauuuuucuu auuguugcgg caauagυguu    60 uauaacacuu ugcuucacac ucaaaagaaa gacagaauga uugaacuuuc auuaau       116

<210> SEQ ID NO 27
<211> LENGTH: 102
<212> TYPE: RNA
<213> ORGANISM: Artificial Sequence
<220> FEATURE:
<223> OTHER INFORMATION: SEQ ID NOs 19-36 are the mRNA transcriptions of
      SEQ ID NOs 1-18.

<400> SEQUENCE: 27
acaccuugua augυguuga agguuuuaau uguuacuuuc cuuυacaauc auauggυuuc     60 caacccacua augυguugg uuaccaacca uacagaguag ua                       102

<210> SEQ ID NO 28
<211> LENGTH: 108
<212> TYPE: RNA
<213> ORGANISM: Artificial Sequence
<220> FEATURE:
<223> OTHER INFORMATION: SEQ ID NOs 19-36 are the mRNA transcriptions of
      SEQ ID NOs 1-18.

<400> SEQUENCE: 28
cuugaaggaa aacagggυaa uuucaaaaau cuuagggaau uugυguuυaa gaauauugau    60 gguuauuuua aaauauauuc uaagcacacg ccuauuaauu uagυgcgu                108

<210> SEQ ID NO 29
<211> LENGTH: 119
<212> TYPE: RNA
<213> ORGANISM: Artificial Sequence
<220> FEATURE:
<223> OTHER INFORMATION: SEQ ID NOs 19-36 are the mRNA transcriptions of
      SEQ ID NOs 1-18.

<400> SEQUENCE: 29
ccuuuucuua uggaccuuga aggaaaacag gguaauuuca aaaaucuuag ggaauuugυg    60 uuuaagaaua uugauggυua uuuuaaaaua uauucuaagc acacgccuau uaauuuagu    119
```

```
<210> SEQ ID NO 30
<211> LENGTH: 123
<212> TYPE: RNA
<213> ORGANISM: Artificial Sequence
<220> FEATURE:
<223> OTHER INFORMATION: SEQ ID NOs 19-36 are the mRNA transcriptions of
      SEQ ID NOs 1-18.

<400> SEQUENCE: 30
ccuuuucuua uggaccuuga aggaaaacag gguaauuuca aaaaucuuag ggaauuugug        60
uuuaagaaua uugaugguua uuuuaaaaua uauucuaagc acacgccuau uaauuuagug       120
cgu                                                                    123

<210> SEQ ID NO 31
<211> LENGTH: 122
<212> TYPE: RNA
<213> ORGANISM: Artificial Sequence
<220> FEATURE:
<223> OTHER INFORMATION: SEQ ID NOs 19-36 are the mRNA transcriptions of
      SEQ ID NOs 1-18.

<400> SEQUENCE: 31
ccuuuucuua uggaccuuga aggaaaacag gguaauuuca aaaaucuuag ggaauuugug        60
uuuaagaaua uugaugguua uuuuaaaaua uauucuaagc acacgccuau uaauuuagug       120
cg                                                                     122

<210> SEQ ID NO 32
<211> LENGTH: 100
<212> TYPE: RNA
<213> ORGANISM: Artificial Sequence
<220> FEATURE:
<223> OTHER INFORMATION: SEQ ID NOs 19-36 are the mRNA transcriptions of
      SEQ ID NOs 1-18.

<400> SEQUENCE: 32
uucacauaug uauuguucuu uuuacccucc agaugaggau gaagaagaag gugauuguga        60
agaagaagag uuugagccau caacucaaua ugaguauggu                            100

<210> SEQ ID NO 33
<211> LENGTH: 102
<212> TYPE: RNA
<213> ORGANISM: Artificial Sequence
<220> FEATURE:
<223> OTHER INFORMATION: SEQ ID NOs 19-36 are the mRNA transcriptions of
      SEQ ID NOs 1-18.

<400> SEQUENCE: 33
gcuucacaua uguauuguuc uuuuuacccu ccagaugagg augaagaaga aggugauugu        60
gaagaagaag aguuugagcc aucaacucaa uaugaguaug gu                         102

<210> SEQ ID NO 34
<211> LENGTH: 118
<212> TYPE: RNA
<213> ORGANISM: Artificial Sequence
<220> FEATURE:
<223> OTHER INFORMATION: SEQ ID NOs 19-36 are the mRNA transcriptions of
      SEQ ID NOs 1-18.

<400> SEQUENCE: 34
uggugaguuu aaauuggcuu cacauaugua uuguucuuuu uacccuccag augaggauga        60
agaagaaggu gauugugaag aagagaguu ugagccauca acucaauaug aguauggu         118
```

<210> SEQ ID NO 35
<211> LENGTH: 113
<212> TYPE: RNA
<213> ORGANISM: Artificial Sequence
<220> FEATURE:
<223> OTHER INFORMATION: SEQ ID NOs 19-36 are the mRNA transcriptions of
      SEQ ID NOs 1-18.

<400> SEQUENCE: 35
uggugaguuu aaauuggcuu cacauaugua uuguucuuuc uacccuccag augaggauga    60
agaagaaggu gauugugaag aagaagaguu ugagccauca acucaauaug agu          113

<210> SEQ ID NO 36
<211> LENGTH: 118
<212> TYPE: RNA
<213> ORGANISM: Artificial Sequence
<220> FEATURE:
<223> OTHER INFORMATION: SEQ ID NOs 19-36 are the mRNA transcriptions of
      SEQ ID NOs 1-18.

<400> SEQUENCE: 36
uggugaguuu aaauuggcuu cacauaugua uuguucuuuc uacccuccag augaggauga    60
agaagaaggu gauugugaag aagaagaguu ugagccauca acucaauaug aguauggu     118

<210> SEQ ID NO 37
<211> LENGTH: 29016
<212> TYPE: DNA
<213> ORGANISM: Artificial Sequence
<220> FEATURE:
<223> OTHER INFORMATION: Based on MT520215.1 as a computational
      reduction vaccine (see Specification for details). This sequences
      is identical to that filed with the original patent.

<400> SEQUENCE: 37
gtaacaaacc aaccaacttt cgatctcttg tagatctgtt ctctaaacga actttaaaat    60
ctgtgtggct gtcactcggc tgcatgctta gtgcactcac gcagtataat taataactaa   120
ttactgtcgt tgacaggaca cgagtaactc gtctatcttc tgcaggctgc ttacggtttc   180
gtccgtgttg cagccgatca tcagcacatc taggtttcgt ccgggtgtga ccgaaaggta   240
agatggagag ccttgtccct ggtttcaacg agaaaacaca cgtccaactc agtttgcctg   300
ttttacaggt tcgcgacgtg ctcgtacgtg gctttggaga ctccgtggag gaggtcttat   360
cagaggcacg tcaacaacgt tcggatgctc gaactgcacc tcatggtcat gttatggttg   420
agctggtagc agaactcgaa ggcattcagt acggtcgtag tggtgagaca cttggtgtcc   480
ttgtccctca tgtgggcgaa ataccagtgg cttaccgcaa ggttcttctt cgtaagaacg   540
gtaataaagg agctggtggc catagttacg gcgccgatct aaagtcattt gacttaggcg   600
acgagcttgg cactgatcct tatgaagatt ttcaagaaaa ctggaacact aaacatagca   660
gtggtgttac ccgtgaactc atgcgtgagc ttaacgagg ggcatacact cgctatgtcg   720
ataacaactt ctgtggccct gatggctacc ctcttgagtg cattaaagac cttctagcac   780
gtgctggtaa agcttcatgc actttgtccg aacaactgga ctttattgac actaagaggg   840
gtgtatactg ctgccgtgaa catgagcatg aaattgcttg gtacacggaa cgttctgaaa   900
agagctatga attgcagaca cctttttgaaa ttaaattggc aaagaaattt gacaccttca   960 atgggaatg tccaaatttt gtattccct taaattccat aatcaagact attcaaccaa   1020
gggttgaaaa gaaaaagctt gatggcttta tgggtagaat tcgatctgtc tatccagttc   1080
cgtcaccaaa tgaatgcaac caaatgtgcc tttcaactct catgaagtgt gatcattgtg   1140

```
gtgaaacttc atggcagacg ggcgattttg ttaaagccac ttgcgaattt tgtggcactg    1200
agaatttgac taaagaaggt gccactactt gtggttactt acccccaaaat gctgttgtta    1260 aaatttattg tccagcatgt cacaattcag aagtaggacc tgagcatagt cttgccgaat    1320
accataatga atctggcttg aaaaccattc ttcgtaaggg tggtcgcact attgcctttg    1380
gaggctgtgt gttctcttat gttggttgcc ataacaagtg tgcctattgg gttccacgtg    1440
ctagcgctaa cataggttgt aaccatacag gtgttgttgg agaaggttcc gaaggtctta    1500
atgacaacct tcttgaaata ctccaaaaag agaaagtcaa catcaatatt gttggtgact    1560
ttaaacttaa tgaagagatc gccattattt tggcatcttt ttctgcttcc acaagtgctt    1620
ttgtggaaac tgtgaaaggt ttggattata agcattcaa acaaattgtt gaatcctgtg    1680
gtaattttaa agttacaaaa ggaaaagcta aaaaaggtgc ctggaatatt ggtgaacaga    1740
aatcaatact gagtcctctt tatgcatttg catcagaggc tgctcgtgtt gtacgatcaa    1800
ttttctcccg cactcttgaa actgctcaaa attctgtgcg tgttttacag aaggccgcta    1860
taacaatact agatggaatt tcacagtatt cactgagact cattgatgct atgatgttca    1920
catctgattt ggctactaac aatctagttg taatggccta cattacaggt ggtgttgttc    1980
agttgacttc gcagtggcta actaacatct ttggcactgt ttatgaaaaa ctcaaaccct    2040
tccttgagtc acctgtgcaa aggaaattaa ggagagtgtt cagacattct ttaagcttgt    2100
aaataaattt ttggctttgt gtgctgactc tatcattatt ggtggagcta aacttaaagc    2160
cttgaattta ggtgaaacat tgtcacgca ctcaaaggga ttgtacagaa agtgtgttaa    2220
atccagagaa gaaactggcc tactcatgcc tctaaaagcc ccaaaagaag ttatcttctt    2280
agagggagaa acacttccca cagaagtgtt aacagaggaa gttgtcttga aaactggtga    2340
tttacaatca ttagaacaac ctactagtga agctgttgaa gctccattgg ttggtacacc    2400
agtttgtatt aacgggctta tgttgctcga aatcaaagac acagaaaagt actgtgccct    2460
tgcacctaat atgatggtaa caaacaatac cttcacactc aaaggcggtg caccaacaaa    2520
ggttactttt ggtgatgaca ctgtgataga agtgcaaggt tacaagagtg tgaatatcac    2580
ttttgaactt gatgaaagga ttgataaagt acttaatgag aagtgctctg cctatacagt    2640
tgaactcggt acagaagtaa atgagttcgc ctgtgttgtg gcagatgctg tcataaaaac    2700
tttgcaacca gtatctgaat tacttacacc actgggcatt gatttagatg agtggagtat    2760
ggctacatac tacttatttg atgagtcatg gtactgaaga tgattaccaa ggtaaacctt    2820
tggaatttgg tgccacttct gctgctcttc aacctgaaga agagcaagaa gaagattggt    2880
tagatgatga tagtcaacaa actgttggtc aacaagacgg cagtgaggac aatcagacaa    2940
ctactattca aacaattgtt gaggttcaac ctcaattaga gatggaactt acaccagttg    3000
ttcagactat tgaagtgaat agttttagtg gttatttaaa acttactgac aatgtataca    3060
ttaaaaatgc agacattgtg gaagaagcta aaaaggtaaa accaacagtg gttgttaatg    3120
cagccaatgt ttaccttaaa catggaggag tgttgcagg agccttaaat aaggctacta    3180
acaatgccat gcaagttgaa tctgatgatt acatagctac taatggacca cttaaagtgg    3240
gtggtagttg tgttttaagc ggacacaatc ttgctaaaca ctgtcttcat gttgtcggcc    3300
caaatgttaa caaaggtgaa gacattcaac ttcttaagag tgcttatgaa aattttaatc    3360
agcacgaagt tctacttgca ccattattat cagctgtat ttttggtgct gaccctatac    3420
attctttaag agtttgtgta gatactgttc gcacaaatgt ctacttagct gtctttgata    3480
```

```
aaaatctcta tgacaaactt gtttcaagct ttttggaaat gaagagtgaa aagcaagttg    3540
aacaaaagat cgctgagatt cctaaagagg aagttaagcc atttataact gaaagtaaac    3600
cttcagttga acagagaaaa caagatgata agaaaatcaa agcttgtgtt gaagaagtta    3660
caacaactct ggaagaaact aagttcctca cagaaaactt gttactttat attgacatta    3720
atggcaatct tcatccagat tctgccactc ttgttagtga cattgacatc actttcttaa    3780
agaaagatgc tccatatata gtgggtgatg ttgttcaaga gggtgtttta actgctgtgg    3840
ttatacctac taaaaaggct ggtggcacta ctgaaatgct agcgaaagct ttgagaaaag    3900
tgccaacaga caattatata accacttacc cgggtcaggg tttaaatggt tacactgtag    3960
aggaggcaaa gacagtgctt aaaaagtgta aagtgccctt ttacattcta ccatctatta    4020
tctctaatga aagcaagaa attcttggaa ctgtttcttg gaatttgcga gaatgcttg     4080 cacatgcaga agaaacacgc aaattaatgc ctgtctgtgt ggaaactaaa gccatagttt    4140
caactataca gcgtaaatat aagggtatta aaatacaaga gggtgtggtt gattatggtg    4200
ctagatttta cttttacacc agtaaaacaa ctgtagcgtc acttatcaac acacttaacg    4260
atctaaatga aactcttgtt acaatgccac ttggctatgt aacacatggc ttaaatttgg    4320
aagaagctgc tcggtatatg agatctctca aagtgccagc tacagtttct gtttcttcac    4380
ctgatgctgt tacagcgtat aatggttatc ttacttcttc ttctaaaaca cctgaagaac    4440
attttattga aaccatctca cttgctggtt cctataaaga ttggtcctat tctggacaat    4500
ctacacaact aggtatagaa tttcttaaga gaggtgataa aagtgtatat tacactagta    4560
atcctaccac attccaccta gatggtgaag ttatcacctt tgacaatctt aagacacttc    4620
tttctttgag agaagtgagg actattaagg tgtttacaac agtagacaac attaacctcc    4680
acacgcaagt tgtggacatg tcaatgacat atggacaaca gtttggtcca acttatttgg    4740
atggagctga tgttactaaa ataaaacctc ataattcaca tgaaggtaaa acattttatg    4800
ttttacctaa tgatgacact ctcgtgttg aggcttttga gtactaccac acaactgatc     4860
ctagttttct gggtaggtac atgtcagcat taaatcacac taaaaagtgg aaataccccac    4920 aagttaatgg tttaacttct attaaatggg cagataacaa ctgttatctt gccactgcat    4980
tgttaacact ccaacaaata gagttgaagt ttaatccacc tgctctacaa gatgcttatt    5040
acagagcaag ggctggtgaa gctgctaact tttgtgcact tatcttagcc tactgtaata    5100
agacagtagg tgagttaggt gatgttagag aaacaatgag ttacttgttt caacatgcca    5160
atttagattc ttgcaaaaga gtcttgaacg tggtgtgtaa acttgtgga caacagcaga    5220 caacccttaa gggtgtagaa gctgttatgt acatgggcac actttcttat gaacaattta    5280
agaaaggtgt tcagataccct tgtacgtgtg gtaaacaagc tacaaaatat ctagtacaac    5340
aggagtcacc ttttgttatg atgtcagcac cacctgctca gtatgaactt aagcatggta    5400
catttacttg tgctagtgag tacactggta attaccagtg tggtcactat aaacatataa    5460
cttctaaaga aactttgtat tgcatagacg gtgctttact tacaaagtcc tcagaataca    5520
aaggtcctat tacggatgtt ttctacaaag aaaacagtta cacaacaacc ataaaaccag    5580
ttacttataa attggatggt gttgtttgta cagaaattga ccctaagttg gacaattatt    5640
ataagaaaga caattcttat ttcacagagc aaccaattga tcttgtacca aaccaaccat    5700
atccaaacgc aagcttcgat aatttttaagt tgtatgtga taatatcaaa tttgctgatg    5760
atttaaacca gttaactggt tataagaaac ctgcttcaag agagcttaaa gttacatttt    5820
tccctgactt aaatggtgat gtggtggcta ttgattataa acactacaca ccctctttta    5880
```

```
agaaaggagc taaattgtta cataaaccta ttgtttggca tgttaacaat gcaactaata    5940
aagccacgta taaaccaaat acctggtgta tacgttgtct ttggagcaca aaaccagttg    6000
aaacatcaaa ttcgtttgat gtactgaagt cagaggacgc gcagggaatg gataatcttg    6060
cctgcgaaga tctaaaacca gtctctgaag aagtagtgga aaatcctacc atacagaaag    6120
acgttcttga gtgtaatgtg aaaactaccg aagttgtagg agacattata cttaaaccag    6180
caaataatag tttaaaaatt acagaagagg ttggccacac agatctaatg gctgcttatg    6240
tagacaattc tagtcttact attaagaaac ctaatgaatt atctagagta ttaggtttga    6300
aaaccccttgc tactcatggt ttagctgctg ttaatagtgt cccttgggat actatagcta    6360
attatgctaa gccttttctt aacaaagttg ttagtacaac tactaacata gttacacggt    6420
gtttaaaccg tgtttgtact aattatatgc cttatttctt tactttattg ctacaattgt    6480
gtacttttac tagaagtaca aattctagaa ttaaagcatc tatgccgact actatagcaa    6540
agaatactgt taagagtgtc ggtaaatttt gtctagaggc ttcatttaat tatttgaagt    6600
cacctaattt ttctaaactg ataaatatta taatttggtt tttactatta agtgtttgcc    6660
taggttcttt aatctactca accgctgctt taggtgtttt aatgtctaat ttaggcatgc    6720
cttcttactg tactggttac agagaaggct atttgaactc tactaatgtc actattgcaa    6780
cctactgtac tgactgcttt tggcttagtt gcagagtggt ttttggcata tattcttttc    6840
actaggtttt tctatgtact tggattggct gcaatcatgc aattgttttt cagctatttt    6900
gcagtacatt ttattagtaa ttcttggctt atgtggttaa taattaatct tgtacaaatg    6960
gccccgattt cagctatggt tagaatgtac atcttctttg catcattta ttatgtatgg    7020
aaaagttatg tgcatgttgt agacggttgt aattcatcaa cttgtatgat gtgttacaaa    7080
cgtaatagag caacaagagt cgaatgtaca actattgtta atggtgttag aaggtccttt    7140
tatgtctatg ctaatggagg taaaggctttt tgcaaactac acaattggaa ttgtgttaat    7200
tgtgatacat tctgtgctgg tagtacattt attagtgatg aagttgcgag agacttgtca    7260
ctacagttta aaagaccaat aaatcctact gaccagtctt cttacatcgt tgatagtgtt    7320
acagtgaaga atggttccat ccatctttac tttgataaag ctggtcaaaa gacttatgaa    7380
agacattctc tctctcattt tgttaactta gacaacctga gagctaataa cactaaaggt    7440
tcattgccta ttaatgttat agtttttgat ggtaaatcaa aatgtgaaga atcatctgca    7500
aaatcagcgt ctgtttacta cagtcagctt atgtgtcaac ctatactgtt actagatcag    7560
gcattagtgt ctgatgttgg tgatagtgcg gaagttgcag ttaaaatgtt tgatgcttac    7620
gttaatacgt tttcatcaac ttttaacgta ccaatggaaa aactcaaaac actagttgca    7680
actgcagaag ctgaacttgc aaagaatgtg tccttagaca atgtcttatc tactttttatt    7740
tcagcagctc ggcaagggtt tgttgattca gatgtagaaa ctaaagatgt tgttgaatgt    7800
cttaaattgt cacatcaatc tgacatagaa gttactggcg atagttgtaa taactatatg    7860
ctcacctata acaaagttga aaacatgaca ccccgtgacc ttggtgcttg tattgactgt    7920
agtgcgcgtc atattaatgc gcaggtagca aaaagtcaca acattgcttt gatatggaac    7980
gttaaagatt tcatgtcatt gtctgaacaa ctacgaaaac aaatacgtag tgctgctaaa    8040
aagaataact tacccttttaa gttgacatgt gcaactacta gacaagttgt taatgttgta    8100
acaacaaaga tagcacttaa gggtggtaaa attgttaata attggttgaa gcagttaatt    8160
aaagttacac ttgtgttcct ttttgttgct gctatttcct atttaataac acctgttcat    8220
```

```
gtcatgtcta aacatactga cttttcaagt gaaatcatag gatacaaggc tattgatggt      8280
ggtgtcactc gtgacatagc atctacagat acttgttttg ctaacaaaca tgctgatttt      8340
gacacatggt ttagccagcg tggtggtagt tatactaatg acaaagcttg cccattgatt      8400
gctgcagtca taacaagaga agtgggtttt gtcgtgcctg gtttgcctgg cacgatatta      8460
cgcacaacta atggtgactt tttgcatttc ttacctagag ttttttagtgc agttggtaac      8520 atctgttaca caccatcaaa acttatagag tacactgact ttgcaacatc agcttgtgtt      8580
ttggctgctg aatgtacaat ttttaaagat gcttctggta agccagtacc atattgttat      8640
gataccaatg tactagaagg ttctgttgct tatgaaagtt tacgccctga cacacgttat      8700
gtgctcatgg atggctctat tattcaattt cctaacaccct accttgaagg ttctgttaga      8760
gtggtaacaa cttttgattc tgagtactgt aggcacggca cttgtgaaag atcagaagct      8820
ggtgtttgtg tatctactag tggtagatgg gtacttaaca atgattatta cagatcttta      8880
ccaggagttt tctgtggtgt agatgctgta aatttactta ctaatatgtt tacaccacta      8940
attcaaccta ttggtgcttt ggacatatca gcatctatag tagctggtgg tattgtagct      9000
atcgtagtaa catgccttgc ctactatttt atgaggttta aagagctttt ggtgaatac      9060 agtcatgtag ttgcctttaa tactttacta ttccttatgt cattcactgt actctgttta      9120
acaccagttt actcattctt acctggtgtt tattctgtta tttacttgta cttgacattt      9180
tatcttacta atgatgtttc tttttagca catattcagt ggatggttat gttcacacct      9240
ttagtacctt tctggataac aattgcttat atcatttgta tttccacaaa gcatttctat      9300
tggttcttta gtaattacct aaagagacgt gtagtcttta atggtgtttc ctttagtact      9360
tttgaagaag ctgcgctgtg cacctttttg ttaaataaag aaatgtatct aaagttgcgt      9420
agtgatgtgc tattacctct tacgcaatat aatagatact agctctttta taataagtac      9480
aagtatttta gtggagcaat ggatacaact agctacagag aagctgcttg ttgtcatctc      9540
gcaaaggctc tcaatgactt cagtaactca ggttctgatg ttctttacca accaccacaa      9600
acctctatca cctcagctgt tttgcagagt ggttttagaa aaatggcatt cccatctggt      9660
aaagttgagg gttgtatggt acaagtaact tgtggtacaa ctacacttaa cggtctttgg      9720
cttgatgacg tagtttactg tccaagacat gtgatctgca cctctgaaga catgcttaac      9780
cctaattatg aagatttact cattcgtaag tctaatcata atttcttggt acaggctggt      9840
aatgttcaac tcagggttat tggacattct atgcaaaatt gtgtacttaa gcttaaggtt      9900
gatacagcca atcctaagac acctaagtat aagtttgttc gcattcaacc aggacagact      9960
ttttcagtgt tagcttgtta caatggttca ccatctggtg tttaccaatg tgctatgagg     10020
cccaatttca ctattaaggg ttcattcctt aatggttcat gtggtagtgt ggttttaac      10080 atagattatg actgtgtctc ttttttgttac atgcaccata tggaattacc aactggagtt     10140
catgctggca cagacttaga aggtaacttt tatggacctt tgttgacag gcaaacagca      10200 caagcagctg gtacggacac aactattaca gttaatgttt tagcttggtt gtacgctgct     10260
gttataaatg gagacaggtg gtttctcaat cgatttacca caactcttaa tgactttaac      10320
cttgtggcta tgaagtacaa ttatgaacct ctaacacaag accatgttga catactagga      10380
cctctttctg ctcaaactgg aattgccgtt ttagatatgt gtgcttcatt aaaagaatta     10440
ctgcaaaatg gtatgaatgg acgtaccata ttgggtagtg ctttattaga agatgaattt      10500 acacctttg atgttgttag acaatgctca ggtgttactt ccaaagtgc agtgaaaaga      10560 acaatcaagg gtacacacca ctggttgtta ctcacaattt tgacttcact tttagtttta     10620
```

```
gtccagagta ctcaatggtc tttgttcttt ttttttatg aaaatgcctt tttacctttt    10680
gctatgggta ttattgctat gtctgctttt gcaatgatgt tgtcaaaca taagcatgca    10740 tttctctgtt tgttttgtt accttctctt gccactgtag cttattttaa tatggtctat    10800
atgcctgcta gttgggtgat gcgtattatg acatggttgg atatggttga tactagtttg    10860
tctggtttta agctaaaaga ctgtgttatg tatgcatcag ctgtagtgtt actaatcctt    10920
atgacagcaa gaactgtgta tgatgatggt gctaggagag tgtggacact tatgaatgtc    10980
ttgacactcg tttataaagt ttattatggt aatgctttag atcaagccat ttccatgtgg    11040
gctcttataa tctctgttac ttctaactac tcaggtgtag ttacaactgt catgtttttg    11100
gccagaggta ttgtttttat gtgtgttgag tattgcccta ttttcttcat aactggtaat    11160
acacttcagt gtataatgct agtttattgt ttcttaggct attttgtac ttgttacttt    11220 ggcctctttt gtttactcaa ccgctacttt agactgactc ttggtgttta tgattactta    11280
gtttctacac aggagtttag atatatgaat tcacagggac tactcccacc caagaatagc    11340
atagatgcct tcaaactcaa cattaaattg ttgggtgttg gtggcaaacc ttgtatcaaa    11400
gtagccactg tacagtctaa aatgtcagat gtaaagtgca catcagtagt cttactctca    11460
gttttgcaac aactcagagt agaatcatca tctaaattgt gggctcaatg tgtccagtta    11520
cacaatgaca ttctcttagc taaagatact actgaagcct ttgaaaaaat ggtttcacta    11580 cttttctgttt tgcttttccat gcagggtgct gtagacataa acaagctttg tgaagaaatg    11640
ctggacaaca gggcaacctt acaagctata gcctcagagt ttagttccct tccatcatat    11700
gcagcttttg ctactgctca agaagcttat gagcaggctg ttgctaatgg tgattctgaa    11760
gttgttctta aaaagttgaa gaagtctttg aatgtggcta aatctgaatt tgaccgtgat    11820
gcagccatgc aacgtaagtt ggaaaagatg gctgatcaag ctatgaccca aatgtataaa    11880
caggctagat ctgaggacaa gagggcaaaa gttactagtg ctatgcagac aatgcttttc    11940
actatgctta gaaagttgga taatgatgca ctcaacaaca ttatcaacaa tgcaagagat    12000
ggttgtgttc ccttgaacat aatacctctt acaacagcag ccaaactaat ggttgtcata    12060
ccagactata acacatataa aaatacgtgt gatggtacaa catttactta tgcatcagca    12120
ttgtgggaaa tccaacaggt tgtagatgca gatagtaaaa ttgttcaact tagtgaaatt    12180
agtatggaca attcacctaa tttagcatgg cctcttattg taacagcttt aagggccaat    12240
tctgctgtca aattacagaa taatgagctt agtcctgttg cactacgaca gatgtcttgt    12300
gctgccggta ctacacaaac tgcttgcact gatgacaatg cgttagctta ctacaacaca    12360
acaaagggag gtaggtttgt acttgcactg ttatccgatt tacaggattt gaaatgggct    12420
agattcccta gagtgatgg aactggtact atctatacag aactggaacc accttgtagg    12480
tttgttacag acacacctaa aggtcctaaa gtgaagtatt tatactttat taaaggatta    12540
aacaacctaa atagaggtat ggtacttggt agtttagctg ccacagtacg tctacaagct    12600
ggtaatgcaa cagaagtgcc tgccaattca actgtattat ctttctgtgc ttttgctgta    12660
gatgctgcta agcttacaa agattatcta gctagtgggg gacaaccaat cactaattgt    12720
gttaagatgt tgtgtacaca cactggtact ggtcaggcaa taacagttac accggaagcc    12780
aatatggatc aagaatcctt tggtggtgca tcgtgttgtc tgtactgccg ttgccacata    12840
gatcatccaa atcctaaagg attttgtgac ttaaaaggta agtatgtaca aatacctaca    12900
acttgtgcta atgaccctgt gggttttaca cttaaaaaca cagtctgtac cgtctgcggt    12960
```

```
atgtggaaag gttatggctg tagttgtgat caactccgcg aacccatgct tcagtcagct   13020
gatgcacaat cgttttttaaa cgggtttgcg gtgtaagtgc agcccgtctt acaccgtgcg   13080
gcacaggcac tagtactgat gtcgtataca gggcttttga catctacaat gataaagtag   13140
ctggttttgc taaattccta aaaactaatt gttgtcgctt ccaagaaaag gacgaagatg   13200
acaatttaat tgattcttac tttgtagtta agagacacac tttctctaac taccaacatg   13260
aagaaacaat ttataattta cttaaggatt gtccagctgt tgctaaacat gacttcttta   13320
agtttagaat agacggtgac atggtaccac atatatcacg tcaacgtctt actaaataca   13380
caatggcaga cctcgtctat gctttaaggc attttgatga aggtaattgt gacacattaa   13440
aagaaatact tgtcacatac aattgttgtg atgatgatta tttcaataaa aaggactggt   13500
atgattttgt agaaaaccca gatatattac gcgtatacgc caacttaggt gaacgtgtac   13560
gccaagcttt gttaaaaaca gtacaattct gtgatgccat gcgaaatgct ggtattgttg   13620
gtgtactgac attagataat caagatctca atggtaactg gtatgatttc ggtgatttca   13680
tacaaaccac gccaggtagt ggagttcctg ttgtagattc ttattattca ttgttaatgc   13740
ctatattaac cttgaccagg gctttaactg cagagtcaca tgttgacact gacttaacaa   13800
agccttacat taagtgggat tgttaaaaat atgacttcac ggaagagagg ttaaaactct   13860
ttgaccgtta ttttaaatat tgggatcaga cataccaccc aaattgtgtt aactgtttgg   13920
atgacagatg cattctgcat tgtgcaaact ttaatgtttt attctctaca gtgttcccac   13980
ctacaagttt tggaccacta gtgagaaaaa tatttgttga tggtgttcca tttgtagttt   14040
caactggata ccacttcaga gagctaggtg ttgtacataa tcaggatgta aacttacata   14100
gctctagact tagttttaag gaattacttg tgtatgctgc tgaccctgct atgcacgctg   14160
cttctggtaa tctattacta gataaacgca ctacgtgctt ttcagtagct gcacttacta   14220
acaatgttgc ttttcaaact gtcaaacccg gtaattttaa caaagacttc tatgactttg   14280
ctgtgtctaa gggtttcttt aaggaaggaa gttctgttga attaaaacac ttcttctttg   14340
ctcaggatgg taatgctgct atcagcgatt atgactatta tcgttataat ctaccaacaa   14400
tgtgtgatat cagacaacta ctatttgtag ttgaagttgt tgataagtac tttgattgtt   14460
acgatggtgg ctgtattaat gctaaccaag tcatcgtcaa caacctagac aaatcagctg   14520
gttttccatt taataaatgg ggtaaggcta gactttatta tgattcaatg agttatgagg   14580
atcaagatgc acttttcgca tatacaaaac gtaatgtcat ccctactata actcaaatga   14640
atcttaagta tgccattagt gcaaagaata gagctcgcac cgtagctggt gtctctatct   14700
gtagtactat gaccaataga cagtttcatc aaaaattatt gaaatcaata gccgccacta   14760
gaggagctac tgtagtaatt ggaacaagca aattctatgg tggttggcac aacatgttaa   14820
aaactgttta tagtgatgta gaaaaccctc accttatggg ttgggattat cctaaatgtg   14880
atagagccat gcctaacatg cttagaatta tggcctcact tgttcttgct cgcaaacata   14940
caacgtgttg tagcttgtca caccgtttct atagattagc taatgagtgt gctcaagtat   15000
tgagtgaaat ggtcatgtgt ggcggttcac tatatgttaa accaggtgga acctcatcag   15060
gagatgccac aactgcttat gctaatagtg ttttttaacat tgtcaagct gtcacggcca   15120 atgttaatgc acttttatct actgatggta acaaaattgc cgataagtat gtccgcaatt   15180
tacaacacag actttatgag tgtctctata gaaatagaga tgttgacaca gactttgtga   15240 atgagttttta cgcatatttg cgtaaacatt tctcaatgat gatactctct gacgatgctg   15300
ttgtgtgttt caatagcact tatgcatctc aaggtctagt ggctagcata aagaacttta   15360
```

```
agtcagttct ttattatcaa aacaatgttt ttatgtctga agcaaaatgt tggactgaga   15420
ctgaccttac taaaggacct catgaatttt gctctcaaca tacaatgcta gttaaacagg   15480
gtgatgatta tgtgtacctt ccttacccag atccatcaag aatcctaggg gccggctgtt   15540
ttgtagatga tatcgtaaaa acagatggta cacttatgat tgaacggttc gtgtctttag   15600
ctatagatgc ttacccactt actaaacatc ctaatcagga gtatgctgat gtctttcatt   15660
tgtacttaca atacataaga aagctacatg atgagttaac aggacacatg ttagacatgt   15720
attctgttat gcttactaat gataacactt caaggtattg ggaacctgag ttttatgagg   15780
ctatgtacac accgcataca gtcttacagg ctgttgggc ttgtgttctt tgcaattcac    15840
agacttcatt aagatgtggt gcttgcatac gtagaccatt cttatgttgt aaatgctgtt   15900
acgaccatgt catatcaaca tcacataaat tagtcttgtc tgttaatccg tatgtttgca   15960
atgctccagg ttgtgatgtc acagatgtga ctcaacttta cttaggaggt atgagctatt   16020
attgtaaatc acataaacca cccattagtt ttccattgtg tgctaatgga caagtttttg   16080
gtttatataa aaatacatgt gttggtagcg ataatgttac tgactttaat gcaattgcaa   16140
catgtgactg gacaaatgct ggtgattaca ttttagctaa cacctgtact gaaagactca   16200 agcttttgc agcagaaacg ctcaaagcta ctgaggagac atttaaactg tcttatggta    16260
ttgctactgt acgtgaagtg ctgtctgaca gagaattaca tctttcatgg gaagttggta   16320
aacctagacc accacttaac cgaaattatg tctttactgg ttatcgtgta actaaaaaca   16380
gtaaagtaca aataggagag tacacctttg aaaaaggtga ctatggtgat gctgttgttt   16440
accgaggtac aacaacttac aaattaaatg ttggtgatta ttttgtgctg acatcacata   16500
cagtaatgcc attaagtgca cctacactag tgccacaaga gcactatgtt agaattactg   16560
gcttataccc aacactcaat atctcagatg agttttctag caatgttgca aattatcaaa   16620
aggttggtat gcaaaagtat tctacactcc agggaccacc tggtactggt aagagtcatt   16680
ttgctattgg cctagctctc tactacccctt ctgctcgcat agtgtataca gcttgctctc  16740
atgccgctgt tgatgcacta tgtgagaagg cattaaaata tttgcctata gataaatgta   16800
gtagaattat acctgcacgt gctcgtgtag agtgttttga taaattcaaa gtgaattcaa   16860
cattagaaca gtatgtcttt tgtactgtaa atgcattgcc tgagacgaca gcagatatag   16920
ttgtctttga tgaaatttca atggccacaa attatgattt gagtgttgtc aatgccagat   16980
tacgtgctaa gcactatgtg tacattggcg accctgctca attacctgca ccacgcacat   17040
tgctaactaa gggcacacta gaaccagaat atttcaattc agtgtgtaga cttatgaaaa   17100
ctataggtcc agacatgttc ctcggaactt gtcggcgttg tcctgctgaa attgttgaca   17160
ctgtgagtgc tttggtttat gataataagc ttaaagcaca taaagacaaa tcagctcaat   17220
gctttaaaat gttttataag ggtgttatca cgcatgatgt ttcatctgca attaacaggc   17280
cacaaatagg cgtggtaaga gaattcctta cacgtaaccc tgcttggaga aaagctgtct   17340
ttatttcacc ttataattca cagaatgctg tagcctcaaa gattttggga ctaccaactc   17400
aaactgttga ttcatcacag ggctcagaat atgactatgt catattcact caaaccactg   17460
aaacagctca ctccttgtaat gtaaacagat ttaatgttgc tattaccaga gcaaaagtag   17520
gcatactttg cataatgtct gatagagacc tttatgacaa gttgcaattt acaagtcttg   17580
aaattccacg taggaatgtg gcaactttac aagctgaaaa tgtaacagga ctcttttaaag  17640 attgtagtaa ggtaatcact gggttacatc ctacacaggc acctacacac ctcagtgttg   17700
```

-continued

```
acactaaatt caaaactgaa ggtttatgtg ttgacatacc tggcatacct aaggacatga    17760
cctatagaag actcatctct atgatgggtt ttaaaatgaa ttatcaagtt aatggttacc    17820
ctaacatgtt tatcacccgc gaagaagcta taagacatgt acgtgcatgg attggcttcg    17880
atgtcgaggg gtgtcatgct actagagaag ctgttggtac caatttacct ttacagctag    17940
gtttttctac aggtgttaac ctagttgctg tacctacagg ttatgttgat acacctaata    18000
atacagattt ttccagagtt agtgctaaac caccgcctgg agatcaattt aaacacctca    18060
taccacttat gtacaaagga cttccttgga atgtagtgcg tataaagatt gtacaaatgt    18120
taagtgacac acttaaaaat ctctctgaca gagtcgtatt tgtcttatgg gcacatggct    18180
ttgagttgac atctatgaag tattttgtga aaataggacc tgagcgcacc tgttgtctat    18240
gtgatagacg tgccacatgc ttttccactg cttcagacac ttatgcctgt tggcatcatt    18300
ctattggatt tgattacgtc tataatccgt ttatgattga tgttcaacaa tggggtttta    18360
caggtaacct acaaagcaac catgatctgt attgtcaagt ccatggtaat gcacatgtag    18420
ctagttgtga tgcaatcatg actaggtgtc tagctgtcca cgagtgcttt gttaagcgtg    18480
ttgactggac tattgaatat cctataattg gtgatgaact gaagattaat gcggcttgta    18540
gaaaggttca acacatggtt gttaaagctg cattattagc agacaaattc ccagttcttc    18600
acgacattgg taaccctaaa gctattaagt gtgtacctca agctgatgta gaatggaagt    18660
tctatgatgc acagccttgt agtgacaaag cttataaaat agaagaatta ttctattctt    18720
atgccacaca ttctgacaaa ttcacagatg gtgtatgcct attttggaat tgcaatgtcg    18780
atagatatcc tgctaattcc attgtttgta gatttgacac tagagtgcta tctaacctta    18840
acttgcctgg ttgtgatggt ggcagtttgt atgtaaataa acatgcattc cacacaccag    18900
cttttgataa aagtgctttt gttaatttaa aacaattacc atttttctat tactctgaca    18960
gtccatgtga gtctcatgga aaacaagtag tgtcagatat agattatgta ccactaaagt    19020
ctgctacgtg tataacacgt tgcaatttag gtggtgctgt ctgtagacat catgctaatg    19080
agtacagatt gtatctcgat gcttataaca tgatgatctc agctggcttt agcttgtggg    19140
tttacaaaca atttgatact tataacctct ggaacacttt tacaagactt cagagtttag    19200
aaaatgtggc ttttaatgtt gtaaataagg acactttga tggacaacag ggtgaagtac    19260
cagtttctat cattaataac actgttaca caaaagttga tggtgttgat gtagaattgt    19320
ttgaaaataa aacaacatta cctgttaatg tagcatttga gctttgggct aagcgcaaca    19380
ttaaaccagt accagaggtg aaaatactca ataatttggg tgtggacatt gctgctaata    19440
ctgtgatctg ggactacaaa agagatgctc cagcacatat atctactatt ggtgtttgtt    19500
ctatgactga catagccaag aaaccaactg aaacgatttg tgcaccactc actgtctttt    19560
ttgatggtag agttgatggt caagtagact tatttagaaa tgcccgtaat ggtgttctta    19620
ttacagaagg tagtgttaaa ggtttacaac catctgtagg tcccaaacaa gctagtctta    19680
atggagtcac attaattgga gaagccgtaa aaacacagtt caattattat aagaaagttg    19740
atggtgttgt ccaacaatta cctgaaactt actttactca gagtagaaat ttacaagaat    19800
ttaaacccag gagtcaaatg gaaattgatt tcttagaatt agctatggat gaattcattg    19860
aacggtataa attagaaggc tatgccttcg aacatatcgt ttatggagat tttagtcata    19920
gtcagttagg tggtttacat ctactgattg gactagctaa acgttttaag gaatcacctt    19980
ttgaattaga agatttttatt cctatggaca gtacagttaa aaactatttc ataacagatg    20040
cgtcaaagtg actattgact atacagaaat ttcatttatg ctttggtgta agatggcca    20100
```

```
tgtagaaaca ttttacccaa aattacaatc tagtcaagcg tggcaaccgg gtgttgctat   20160
gcctaatctt tacaaaatgc aaagaatgct attagaaaag tgtgaccttc aaaattatgg   20220
tgatagtgca acattaccta aaggcataat gatgaatgtc gcaaaatata ctcaactgtg   20280
tcaatattta aacacattaa cattagctgt accctataat atgagagtta tacattttgg   20340
tgctggttct gataaaggag ttgcaccagg tacagctgtt ttaagacagt ggttgcctac   20400
gggtacgctg cttgtcgatt cagatcttaa tgactttgtc tctgatgcag attcaacttt   20460
gattggtgat tgtgcaactg tacatacagc taataaatgg gatctcatta ttagtgatat   20520
gtacgaccct aagactaaaa atgttacaaa agaaaatgac tctaaagagg ttttttcac   20580 ttacatttgt gggtttatac aacaaaagct agctcttgga ggttccgtgg ctataaagat   20640
aacagaacat tcttggaatg ctgatcttta aagctcatg ggacacttcg catggtggac   20700
agcctttgtt actaatgtga atgcgtcatc atctgaagca ttttaattg gatgtaatta   20760 tcttggcaaa ccacgcgaac aaatagatgg ttatgtcatg catgcaaatt acatattttg   20820
gaggaataca aatccaattc agttgtcttc ctattcttta tttgacatga gtaaatttcc   20880
ccttaaatta aggggtactg ctgttatgtc tttaaaagaa ggtcaaatca atgatatgat   20940
tttatctctt cttagtaaag gtagacttat aattagagaa aacaacagag ttgttatttc   21000
tagtgatgtt cttgttaaca actaaacgaa caatgtttgt ttttcttgtt ttattgccac   21060
tagtctctag tcagtgtgtt aatcttacaa ccagaactca attacccccct gcatacacta   21120 attctttcac acgtggtgtt tattaccctg acaaagtttt cagatcctca gttttacatt   21180
caactcagga cttgttctta ccttcttttt ccaatgttac ttggttccat gctatacatg   21240
tctctgggac caatggtact aagaggtttg ataacctcgt cctaccattt aatgatggtg   21300
tttattttgc ttccactgag aagtctaaca taataagagg ctggattttt ggtactactt   21360
tagattcgaa gacccagtcc ctacttattg ttaataacgc tactaatgtt gttattaaag   21420
tctgtgaatt tcaattttgt aatgatccat ttttgggtgt ttattaccac aaaaacaaca   21480
aaagttggat ggaaagtgag ttcagagttt attctagtgc gaataattgc acttttgaat   21540
atgtctctca gccttttctt atggacgatc tccctcaggg ttttttcggct ttagaaccat   21600 tggtagattt gccaataggt attaacatca ctaggtttca aactttactt gctttacata   21660
gaagttattt gactcctggt gattcttctt caggttggac agctggtgct gcagcttatt   21720
atgtgggtta tcttcaacct aggactttttc tattaaaata taatgaaaat ggaaccatta   21780
cagatgctgt agactgtgca cttgaccctc tctcagaaac aaagtgtacg ttgaaatcct   21840
tcactgtaga aaaggaatc tatcaaactt ctaactttag agtccaacca acagaatcta   21900
ttgttagatt tcctaatatt acaaacttgt gccctttggg tgaagttttt aacgccacca   21960
gatttgcatc tgtttatgct tggaacagga agagaatcag caactgtgtt gctgattatt   22020
ctgtcctata taattccgca tcatttttcca cttttaagtg ttatgagtg tctcctacta   22080 aattaaatga tctctgcttt actaatgtct atgcagattc atttgtaatt agaggtgatg   22140
aagtcagaca aatcgctcca gggcaaactg gaaagattgc tgattataat tataaattac   22200
cagatgattt tacaggctgc gttatagctt ggaattctaa caatcttgat tctaaggttg   22260
gtggtaatta taattacctg tatagattgt ttaggaagtc taatctcaaa cctttgaga   22320 gagatatttc aactgaaatc tatcaggccg gtagcgtact tcttttgaa cttctacatg   22380 caccagcaac tgtttgtgga cctaaaaagt ctactaattt ggttaaaaac aaatgtgtca   22440
```

```
atttcaactt caatggttta acaggcacag gtgttcttac tgagtctaac aaaaagtttc   22500
tgcctttcca acaatttggc agagacattg ctgacactac tgatgctgtc cgtgatccac   22560
agacacttga gattcttgac attacaccat gttcttttgg tggtgtcagt gttataacac   22620
caggaacaaa tacttctaac caggttgctg ttctttatca ggatgttaac tgcacagaag   22680
tccctgttgc tattcatgca gatcaactta ctcctacttg gcgtgtttat tctacaggtt   22740
ctaatgtttt tcaaacacgt gcaggctgtt taatagggc tgaacatgtc aacaactcat   22800
atgagtgtga catacccatt ggtgcaggta tatgcgctag ttatcagact cagactaatt   22860
ctcctcggcg ggcacgtagt gtagctagtc aatccatcat tgcctacact atgtcacttg   22920
gtgcagaaaa ttcagttgct tactctaata actctattgc catacccaca aatttacta   22980 ttagtgttac cacagaaatt ctaccagtgt ctatgaccaa gacatcagta gattgtacaa   23040
tgtacatttg tggtgattca actgaatgca gcaatctttt gttgcaatat ggcagttttt   23100
gtacacaatt aaaccgtgct ttaactggaa tagctgttga acaagacaaa aacacccaag   23160 aagttttgc acaagtcaaa caatttaca aaacaccacc aattaaagat tttggtggtt   23220 ttaattttc acaatatta ccagatccat caaaaccaag caagaggtca tttattgaag   23280 atctacttt caacaaagtg acacttgcag atgctggctt catcaaacaa tatggtgatt   23340
gccttggtga tattgctgct agagacctca tttgtgcaca aaagttaac ggccttactg   23400 ttttgccacc tttgctcaca gatgaaatga ttgctcaata cacttctgca ctgttagcgg   23460
gtacaatcac ttctggttgg acctttggtg caggtgctgc attacaaata ccatttgcta   23520
tgcaaatggc ttataggttt aatggtattg agttacaca gaatgttctc tatgagaacc   23580
aaaaattgat tgccaaccaa tttaatagtg ctattggcaa aattcaagac tcactttctt   23640
ccacagcaag tgcacttgga aaacttcaag atgtggtcaa ccaaaatgca caagctttaa   23700
acacgcttgt taaacaactt agctccaatt ttggtgcaat ttcaagtgtt ttaaatgata   23760
tcctttcacg tcttgacaaa gttgaggctg aagtgcaaat tgataggttg atcacaggca   23820
gacttcaaag tttgcagaca tatgtgactc aacaattaat tagagctgca gaaatcagag   23880
cttctgctaa tcttgctgct actaaaatgt cagagtgtgt acttggacaa tcaaaaagag   23940
ttgatttttg tggaaagggc tatcatctta tgtccttccc tcagtcagca cctcatggtg   24000
tagtcttctt gcatgtgact tatgtccctg cacaagaaaa gaacttcaca actgctcctg   24060
ccatttgtca tgatggaaaa gcacactttc ctcgtgaagg tgtctttgtt tcaaatggca   24120
cacactggtt tgtaacacaa aggaattttt atgaaccaca aatcattact acagacaaca   24180
catttgtgtc tggtaactgt gatgttgtaa taggaattgt caacaacaca gtttatgatc   24240
ctttgcaacc tgaattagac tcattcaagg aggagttaga taaatatttt aagaatcata   24300
catcaccaga tgttgattta ggtgacatct ctggcattaa tgcttcagtt gtaaacattc   24360
aaaaagaaat tgaccgcctc aatgaggttg ccaagaattt aaatgaatct ctcatcgatc   24420
tccaagaact tggaaagtat gagcagtata taaaatggcc atggtacatt tggctaggtt   24480
ttatagctgg cttgattgcc atagtaatgg tgacaattat gctttgctgt atgaccagtt   24540
gctgtagttg tctcaagggc tgttgttctt gtggatcctg ctgcaaattt gatgaagacg   24600
actctgagcc agtgctcaaa ggagtcaaat tacattacac ataaacgaac ttatggattt   24660
gtttatgaga atcttcacaa ttggaactgt aactttgaag caaggtgaaa tcaaggatgc   24720
tactccttca gattttgttc gcgctactgc aacgataccg atacaagcct cactccctt    24780 cggatggctt attgttggcg ttgcacttct tgctgttttt cagagcgctt ccaaaatcat   24840
```

```
aaccctcaaa aagagatggc aactagcact ctccaagggt gttcactttg tttgcaactt   24900
gctgttgttg tttgtaacag tttactcaca ccttttgctc gttgctgctg gccttgaagc   24960
cccttttctc tatctttatg ctttagtcta cttcttgcag agtataaact ttgtaagaat   25020
aataatgagg ctttggcttt gctggaaatg ccgttccaaa aacccattac tttatgatgc   25080
caactatttt ctttgctggc atactaattg ttacgactat tgtatacctt acaatagtgt   25140
aacttcttca attgtcatta cttcaggtga tggcacaaca agtcctattt ctgaacatga   25200
ctaccagatt ggtggttata ctgaaaaatg ggaatctgga gtaaaagact gtgttgtatt   25260
acacagttac ttcacttcag actattacca gctgtactca actcaattga gtacagacac   25320
tggtgttgaa catgttacct tcttcatcta caataaaatt gttgatgagc tgaagaaca    25380 tgtccaaatt cacacaatcg acgtttcatc cggagttgtt aatccagtaa tggaaccaat   25440
ttatgatgaa ccgacgacga ctactagcgt gcctttgtaa gcacaagctg atgagtacga   25500
acttatgtac tcattcgttt cggaagagac aggtacgtta atagttaata gcgtacttct   25560
ttttcttgct ttcgtggtat tcttgctagt tacactagcc atccttactg cgcttcgatt   25620
gtgtgcgtac tgctgcaata ttgttaacgt gagtcttgta aaaccttctt tttacgttta   25680
ctctcgtgtt aaaaatctga attcttctag agttcctgat cttctggtct aaacgaacta   25740
aatattatat tagtttttct gtttggaact ttaattttag ccatggcaga ttccaacggt   25800
actattaccg ttgaagagct aaaaagctc cttgaacaat ggaacctagt aataggtttc    25860
ctattcctta catggatttg tcttctacaa tttgcctatg ccaacaggaa taggttttg    25920 tatataatta agttaatttt cctctggctg ttatggccag taactttagc ttgttttgtg   25980
cttgctgctg tttacagaat aaattggatc accggtggaa ttgctatcgc aatggcttgt   26040
cttgtaggct tgatgtggct cagctacttc attgcttctt tcagactgtt tgcgcgtacg   26100
cgttccatgt ggtcattcaa tccagaaact aacattcttc tcaacgtgcc actccatggc   26160
actattctga ccagaccgct tctagaaagt gaactcgtaa tcggagctgt gatccttcgt   26220
ggacatcttc gtattgctgg acaccatcta ggacgctgtg acatcaagga cctgcctaaa   26280
gaaatcactg ttgctacatc acgaacgctt tcttattaca aattgggagc ttcgcagcgt   26340
gtagcaggtg actcaggttt tgctgcatac agtcgctaca ggattggcaa ctataaatta   26400
aacacagacc attccagtag cagtgacaat attgctttgc ttgtacagta agtgacaaca   26460
gatgtttcat ctcgttgact ttcaggttac tatagcagag atattactaa ttattatgag   26520
gacttttaaa gtttccattt ggaatcttga ttacatcata aacctcataa ttaaaaattt   26580
atctaagtca ctaactgaga ataaatattc tcaattagat gaagagcaac caatggagat   26640
tgattaaacg aacatgaaaa ttattctttt cttggcactg ataacactcg ctacttgtga   26700
gctttatcac taccaagagt gtgttagagg tacaacagta cttttaaaag aaccttgctc   26760
ttctggaaca tacgagggca attcaccatt tcatcctcta gctgataaca atttgcact    26820 gacttgcttt agcactcaat ttgcttttgc ttgtcctgac ggcgtaaaac acgtctatca   26880
gttacgtgcc agatcagttt cacctaaact gttcatcagt gacttctatt tgtgcttttt   26940
agcctttctg ctattccttg ttttaattat gcttattatc ttttggttct cacttgaact   27000
gcaagatcat aatgaaactt gtcacgccta aacgaacatg aaatttcttg ttttcttagg   27060
aatcatcaca actgtagctg catttcacca agaatgtagt ttacagtcat gtactcaaca   27120
tcaaccatat gtagttgatg acccgtgtcc tattcacttc tattctaaat ggtatattag   27180
```

```
agtaggagct agaaaatcag cacctttaat tgaattgtgc gtggatgagg ctggttctaa   27240
atcacccatt cagtcatcg atatcggtaa ttatacagtt tcctgtttac cttttacaat    27300
taattgccag gaacctaaat tgggtagtct tgtagtgcgt tgttcgttct atgaagactt   27360
tttagagtat catgacgttc gtgttgtttt agatttcatc taaacgaaca aactaaaatg   27420
tctgataatg gaccccaaaa tcagcgaaat gcaccccgca ttacgtttgg tggaccctca   27480
gattcaactg gcagtaacca gaatggagaa cgcagtgggg cgcgatcaaa acaacgtcgg   27540
ccccaaggtt tacccaataa tactgcgtct tggttcaccg ctctcactca acatggcaag   27600
gaagacctta aattccctcg aggacaaggc gttccaatta acaccaatag cagtccagat   27660
gaccaaattg gctactaccg aagagctacc agacgaattc gtggtggtga cggtaaaatg   27720
aaagatctca gtccaagatg gtatttctac tacctaggaa ctgggccaga agctggactt   27780
ccctatggtg ctaacaaaga cggcatcata tgggttgcaa ctgagggagc cttgaataca   27840
ccaaaagatc acattggcac cgcaatcct gctaacaatg ctgcaatcgt gctacaactt    27900
cctcaaggaa caacattgcc aaaaggcttc tacgcagaag ggagcagagg cggcagtcaa   27960
gcctcttctc gttcctcatc acgtagtcgc aacagttcaa gaaattcaac tccaggcagc   28020
agtaggggaa cttctcctgc tagaatggct ggcaatggcg gtgatgctgc tcttgctttg   28080
ctgctgcttg acagattgaa ccagcttgag agcaaaatgt ctggtaaagg ccaacaacaa   28140
caaggccaaa ctgtcactaa gaaatctgct gctgaggctt ctaagaagcc tcggcaaaaa   28200
cgtactgcca ctaaagcata caatgtaaca caagctttcg gcagacgtgg tccagaacaa   28260
acccaaggaa attttgggga ccaggaacta atcagacaag gaactgatta caaacattgg   28320
ccgcaaattg cacaatttgc ccccagcgct tcagcgttct tcggaatgtc gcgcattggc   28380
atggaagtca caccttcggg aacgtggttg acctacacag gtgccatcaa attggatgac   28440
aaagatccaa atttcaaaga tcaagtcatt ttgctgaata agcatattga cgcatacaaa   28500
acattcccac caacagagcc taaaaaggac aaaaagaaga aggctgatga aactcaagcc   28560
ttaccgcaga cacagaagaa acagcaaact gtgactcttc ttcctgctgc agatttggat   28620
gatttctcca acaattgca acaatccatg agcagtgctg actcaactca ggcctaaact    28680
catgcagacc acacaaggca gatgggctat ataaacgttt tcgcttttcc gtttacgata   28740
tatagtctac tcttgtgcag aatgaattct cgtaactaca tagcacaagt agatgtagtt   28800
aactttaatc tcacatagca atctttaatc agtgtgtaac attagggagg acttgaaaga   28860
gccaccacat tttcaccgag gccacgcgga gtacgatcga gtgtacagtg aacaatgcta   28920
gggagagctg cctatatgga agagccctaa tgtgtaaaat taattttagt agtgctatcc   28980
ccatgtgatt ttaatagctt cttaggagaa tgacaa                             29016
```

Having described my invention herein, I claim:

1. A composition comprising SEQ ID NOs: 1-18.
2. A composition comprising SEQ ID NOs: 19-36.
3. A composition comprising a SARS-COV-2 genome whose DNA equivalent is SEQ ID NO: 37, in which SEQ ID NOs: 1-18 have been removed.

* * * * *